United States Patent
Pai et al.

(10) Patent No.: US 12,049,437 B2
(45) Date of Patent: Jul. 30, 2024

(54) DIISOCYANATE COMPOSITION, PREPARATION METHOD THEREOF AND OPTICAL MATERIAL USING SAME

(71) Applicants: SKC CO., LTD., Gyeonggi-do (KR); WOORI FINE CHEM CO., LTD., Gyeonggi-do (KR)

(72) Inventors: Jaeyoung Pai, Gyeonggi-do (KR); Jeongmoo Kim, Gyeonggi-do (KR); Hyuk Hee Han, Gyeonggi-do (KR); Jung Hwan Myung, Gyeonggi-do (KR); Myung-Ok Kyun, Gyeonggi-do (KR); Jooyoung Jung, Gyeonggi-do (KR)

(73) Assignees: SK PUCORE CO., LTD., Ulsan (KR); WOORI FINE CHEM CO., LTD., Gyeonggi-Do (KR)

( * ) Notice: Subject to any disclaimer, the term of this patent is extended or adjusted under 35 U.S.C. 154(b) by 507 days.

(21) Appl. No.: 17/111,688

(22) Filed: Dec. 4, 2020

(65) Prior Publication Data
US 2021/0171451 A1   Jun. 10, 2021

(30) Foreign Application Priority Data

Dec. 6, 2019  (KR) .................. 10-2019-0161447
Dec. 6, 2019  (KR) .................. 10-2019-0161448
Dec. 6, 2019  (KR) .................. 10-2019-0161449

(51) Int. Cl.
C07C 265/08  (2006.01)
C07C 263/20  (2006.01)
G02B 1/04    (2006.01)

(52) U.S. Cl.
CPC .......... *C07C 265/08* (2013.01); *C07C 263/20* (2013.01); *G02B 1/041* (2013.01)

(58) Field of Classification Search
CPC ........ C07C 265/08; G02B 1/041; C08G 18/71
USPC ....................................................... 560/338
See application file for complete search history.

(56) References Cited

U.S. PATENT DOCUMENTS

| | | |
|---|---|---|
| 2018/0334531 A1 | 11/2018 | Shin et al. |
| 2020/0102268 A1 | 4/2020 | Park et al. |

FOREIGN PATENT DOCUMENTS

| | | |
|---|---|---|
| CN | 1931834 A | 3/2007 |
| CN | 106674056 A | 5/2017 |
| CN | 106748887 A | 5/2017 |
| CN | 108689883 A | 10/2018 |
| CN | 110114339 A | 8/2019 |
| EP | 3470 393 * | 1/2019 |
| EP | 3444236 A1 | 2/2019 |
| EP | 3564212 A1 | 11/2019 |
| JP | S61-194057 A | 8/1986 |
| JP | H10-017537 A | 1/1998 |
| JP | 2018-070611 A | 5/2018 |
| KR | 10-1842254 B1 | 3/2018 |
| KR | 10-2018-0125871 A | 11/2018 |
| KR | 10-2019-0086257 A | 7/2019 |
| KR | 10-2019-0129819 A | 11/2019 |
| WO | WO2018168419 * | 1/2018 |
| WO | 2019/050236 A1 | 3/2019 |

OTHER PUBLICATIONS

WO2018168419-translation, 2018.*
Extended Search Report issued by the European Patent Office on May 3, 2021.
Office Action issued by the Korean Patent Office on May 25, 2021.
Office Action for application 202011431226.9 issued by the Chinese Intellectual Property Office on May 17, 2022.
Office Action issued by the Japanese Patent Office on Jan. 25, 2022.
Office Action issued by the Korean Intellectual Property Office on Jan. 26, 2022.

\* cited by examiner

*Primary Examiner* — Ana Z Muresan

(74) *Attorney, Agent, or Firm* — IP & T GROUP LLP

(57) ABSTRACT

The diisocyanate composition according to an embodiment of the present invention comprises, in the composition, a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof. It is possible to improve the optical characteristics by preventing the occurrence of yellowing, striae, and cloudiness and to enhance the mechanical properties such as impact resistance at the same time. Thus, it can be advantageously used to prepare an optical material of high quality.

6 Claims, 1 Drawing Sheet

[Fig. 1A]
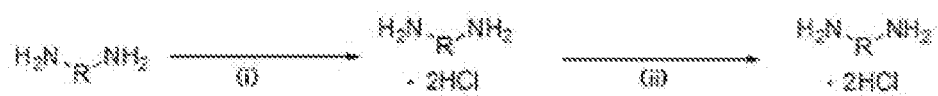
[Fig. 1B]
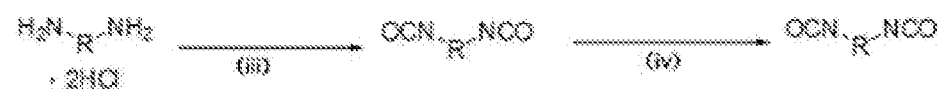
[Fig. 2]
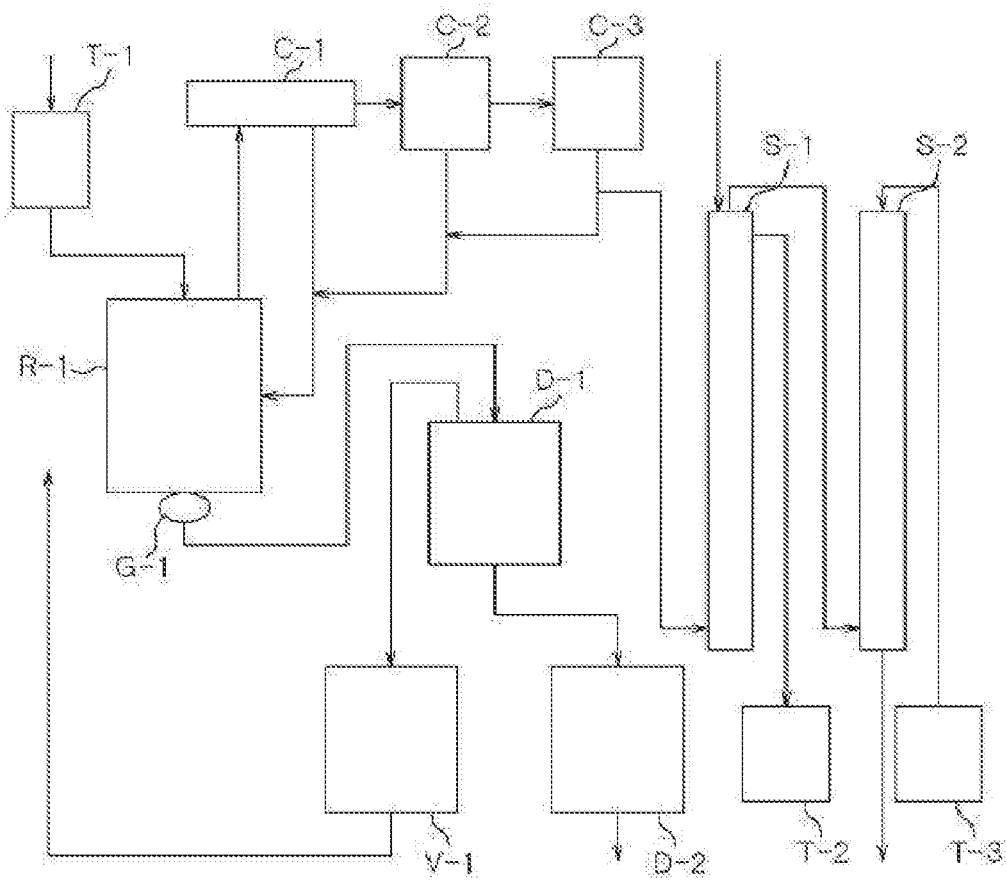

DIISOCYANATE COMPOSITION, PREPARATION METHOD THEREOF AND OPTICAL MATERIAL USING SAME

The present application claims priority of Korean patent application numbers 10-2019-0161447 filed on Dec. 6, 2019, 10-2019-0161448 filed on Dec. 6, 2019 and 10-2019-0161449 filed on Dec. 6, 2019. The disclosure of each of the foregoing applications is incorporated herein by reference in its entirety.

TECHNICAL FIELD

Embodiments relate to a diisocyanate composition, a process for preparing the same, and an optical material using the same. More specifically, the embodiments relate to a diisocyanate composition, which comprises, in the composition, a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof, a process for preparing the same, and an optical material using the same.

BACKGROUND ART

Since plastics optical materials are lightweight, hardly breakable, and excellent in dyeability as compared with optical materials made of inorganic materials such as glass, plastic materials of various resins are widely used as optical materials for eyeglass lenses, camera lenses, and the like. In recent years, there has been an increased demand for higher performance of optical materials, particularly in terms of high transparency, high refractive index, low specific gravity, high thermal resistance, high impact resistance, and the like.

Polythiourethanes are widely used as an optical material by virtue of their excellent optical characteristics and excellent mechanical properties. A polythiourethane may be prepared by reacting a thiol and an isocyanate. Lenses made from a polythiourethane are widely used by virtue of their high refractive index, lightweight, and relatively high impact resistance.

Isocyanates used as a raw material of a polythiourethane are capable of producing polythiourethanes having different structures depending on the number and position of the functional groups in the isocyanates. Thus, the isocyanates have a significant impact on the physical properties of a product produced from the polythiourethane. Accordingly, a certain kind of isocyanate that can impart the desired properties to a final product is used.

In particular, since xylylene diisocyanate (XDI) has both characteristics of alicyclic isocyanates (e.g., resistance to yellowing, readily controllable reactivity, and the like) and those of aliphatic isocyanates (e.g., excellent mechanical properties, high refractive indices, and the like), it is advantageously used as an optical material.

Xylylene diisocyanate is classified into orthoxylylene diisocyanate (o-XDI), metaxylylene diisocyanate (m-XDI), and paraxylylene diisocyanate (p-XDIA) depending on the relative position of the diisocyanate groups. m-XDI among these is the most widely used as a raw material for an optical lens since it is suitable for the physical properties of an optical lens and available in the market.

However, even when m-XDI is used for an optical material, there is a limit in achieving satisfactory optical characteristics due to the occurrence of striae, cloudiness, or yellowing in the optical material. Even if the optical characteristics in terms of stria, cloudiness, or yellow index are satisfied, the impact resistance may be deteriorated. Thus, it is still difficult to satisfy them at the same time.

Accordingly, in order to achieve an optical material of high quality by simultaneously enhancing the optical characteristics and mechanical characteristics, there is an urgent demand for developing a diisocyanate composition having a specific range of composition or a process for preparing the same.

DETAILED DESCRIPTION OF THE INVENTION

Technical Problem

The present invention is designed to solve the problems of the prior art. It has been discovered that the physical properties of an optical material can be effectively satisfied when a benzyl isocyanate having a methyl group, an aromatic compound having a halogen group, a benzyl isocyanate having an ethyl group, or a combination thereof is employed in a specific amount in the diisocyanate composition.

Accordingly, an object of the embodiments is to provide a diisocyanate composition in which the content of a benzyl isocyanate having a methyl group, an aromatic compound having a halogen group, or a benzyl isocyanate having an ethyl group is adjusted in the composition, thereby preventing the occurrence of striae and cloudiness in an optical material, lowering the yellow index, and enhancing the impact resistance and transmittance, and a process for preparing the same.

Another object of the embodiments is to provide a polymerizable composition for an optical material, which comprises the above diisocyanate composition.

Still another object of the embodiments is to provide an optical material formed by curing the polymerizable composition for an optical material.

Solution to the Problem

According to an embodiment, there is provided a diisocyanate composition, which comprises, in the composition, a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof.

According to another embodiment, there is provided a process for preparing a diisocyanate composition, which comprises obtaining a diamine hydrochloride composition; treating the diamine hydrochloride composition; and obtaining a diisocyanate composition using the treated diamine hydrochloride composition and triphosgene, wherein the content of a benzyl isocyanate having a methyl group is 5 ppm to 200 ppm, the content of an aromatic compound having a halogen group is 5 ppm to 1,000 ppm, or the content of a benzyl isocyanate having an ethyl group is 1 ppm to 1,000 ppm in the diisocyanate composition.

According to an embodiment, there is provided an optical material formed by curing a polymerizable composition for an optical material comprising a diisocyanate composition, wherein the diisocyanate composition comprises a diisocyanate and a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof.

Advantageous Effects of the Invention

According to the embodiments, an optical lens of high quality can be prepared by adjusting the composition of a diisocyanate composition used in the production of a polythiourethane-based optical lens.

That is, in order to achieve an optical material of high quality, a diisocyanate composition comprising a specific content of a benzyl isocyanate having a methyl group, an aromatic compound having a halogen group, or a benzyl isocyanate having an ethyl group is used, thereby improving the optical characteristics by preventing the occurrence of yellowing, striae, and cloudiness and enhancing the mechanical properties such as impact resistance at the same time.

In addition, in the process for preparing a diisocyanate composition according to an embodiment of the present invention, phosgene gas, which is highly toxic and has difficulties in storage and management, is not used. Instead, triphosgene, which is less toxic and does not require a separate cooling storage apparatus since it is solid at room temperature, is used; thus, it is excellent in the handling convenience and processability; and the content of a benzyl isocyanate having an ethyl group can be conveniently controlled to a specific range. In addition, in the process for preparing a diisocyanate according to the above embodiment, an aqueous hydrochloric acid solution, without the use of hydrogen chloride gas, is used to prepare a diamine hydrochloride as an intermediate. Since the reaction can be carried out even at atmospheric pressure, an additional apparatus for high-temperature heating and cooling is not required, and the yield can be enhanced.

BRIEF DESCRIPTION OF THE DRAWINGS

FIG. 1A and FIG. 1B schematically show the process for preparing a diisocyanate composition according to an embodiment.

FIG. 2 shows an example of the process equipment for the reaction of a diamine hydrochloride and triphosgene.

REFERENCE NUMERALS OF THE DRAWINGS

T-1: first tank, T-2: second tank, T-3: third tank
R-1: reactor, D-1: first distiller, D-2: second distiller
C-1: first condenser, C-2: second condenser, C-3: third condenser
S-1: first scrubber, S-2: second scrubber
G-1: viewing window, V-1: solvent recovery apparatus.

BEST MODE FOR CARRYING OUT THE INVENTION

Throughout the present specification, when a part is referred to as "comprising" an element, it is understood that other elements may be comprised, rather than other elements are excluded, unless specifically stated otherwise.

In addition, all numbers and expression related to the physical properties, contents, dimensions, and the like used herein are to be understood as being modified by the term "about," unless otherwise indicated.

In the present specification, an "amine" refers to a compound having one or more amine groups at the terminal, and a "diamine" refers to a compound having two amine groups at the terminal. They may have a wide variety of structures depending on the skeleton of an aliphatic chain, an aliphatic ring, and an aromatic ring. Specific examples of the diamine include xylylenediamine (XDA), hexamethylenediamine (HDA), 2,2-dimethylpentanediamine, 2,2,4-trimethylhexanediamine, butenediamine, 1,3-butadiene-1,4-diamine, 2,4,4-trimethylhexamethylenediamine, bis(aminoethyl)carbonate, 4,4'-methylenediamine (MDA), bis(aminoethyl) ether, bis(aminoethyl)benzene, bis(aminopropyl)benzene, α,α,α',α'-tetramethylxylylenediamine, bis(aminobutyl)benzene, bis(aminomethyl)naphthalene, bis(aminomethyl)diphenyl ether, bis(aminoethyl)phthalate, 2,6-di(aminomethyl)furan, hydrogenated xylylenediamine (H6XDA), dicyclohexylmethanediamine, cyclohexanediamine, methylcyclohexanediamine, isophoronediamine (IPDA), dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl) tricyclodecane, 4,8-bis(aminomethyl)tricyclodecane, 4,9-bis (aminomethyl)tricyclodecane, norbornenediamine (NBDA), bis(aminomethyl) sulfide, bis(aminoethyl) sulfide, bis(aminopropyl) sulfide, bis(aminohexyl) sulfide, bis(aminomethyl) sulfone, bis(aminomethyl) disulfide, bis(aminoethyl) disulfide, bis(aminopropyl) disulfide, bis(aminomethylthio) methane, bis(aminoethylthio)methane, bis(aminoethylthio) ethane, and bis(aminomethylthio)ethane. More specifically, the diamine may be at least one selected from the group consisting of xylylenediamine (XDA), norbornenediamine (NBDA), hydrogenated xylylenediamine (H6XDA), isophoronediamine (IPDA), and hexamethylenediamine (HDA). The xylylenediamine (XDA) includes orthoxylylenediamine (o-XDA), metaxylylenediamine (m-XDA), and paraxylylenediamine (p-XDA).

In the present specification, an "isocyanate" refers to a compound having an NCO group, a "diisocyanate" refers to a compound having two NCO groups at the terminal. They may have a wide variety of structures depending on the skeleton of an aliphatic chain, an aliphatic ring, and an aromatic ring. Specific examples of the diamine include xylylene diisocyanate (XDI), hexamethylene diisocyanate (HDI), 2,5-bis(isocyanatomethyl)-bicyclo[2.2.1]heptane, 2,6-bis(isocyanatomethyl)-bicyclo[2.2.1]heptane, hydrogenated xylylene diisocyanate (H6XDI), dicyclohexylmethane diisocyanate, isophorone diisocyanate (IPDI), 1,2-diisocyanatobenzene, 1,3-diisocyanatobenzene, 1,4-diisocyanatobenzene, 2,4-diisocyanatotoluene, ethylphenylene diisocyanate, dimethylphenylene diisocyanate, biphenyl diisocyanate, toluidine diisocyanate, 4,4'-methylenebis(phenylisocyanate) (MDI), 1,2-bis(isocyanatomethyl)benzene, 1,3-bis(isocyanatomethyl)benzene, 1,4-bis(isocyanatomethyl)benzene, 1,2-bis(isocyanatoethyl)benzene, 1,3-bis (isocyanatoethyl)benzene, 1,4-bis(isocyanatoethyl)benzene, α,α,α',α'-tetramethylxylylene diisocyanate, bis(isocyanatomethyl)naphthalene, bis(isocyanatomethylphenyl) ether, norbornene diisocyanate (NBDI), bis(isocyanatoethyl) sulfide, bis(isocyanatoethyl) sulfide, bis(isocyanatopropyl) sulfide, 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, and 2,5-diisocyanatomethyl-1,4-dithiane. More specifically, the diisocyanate may be at least one selected from the group consisting of xylylene diisocyanate (XDI), norbornene diisocyanate (NBDI), hydrogenated xylylene diisocyanate (H6XDI), isophorone diisocyanate (IPDI), and hexamethylene diisocyanate (HDI). The xylylene diisocyanate (XDI) includes orthoxylylene diisocyanate (o-XDI), metaxylylene diisocyanate (m-XDI), and paraxylylene diisocyanate (p-XDIA).

In the present specification, as is well known, a "composition" may refer to a form in which two or more chemical components are mixed or combined in a solid, liquid, and/or gas phase while generally maintaining their respective unique properties.

The compounds used in each reaction step according to the above embodiment (e.g., triphosgene) or the compounds obtained as a result of the reaction (e.g., diamine hydrochloride, diisocyanate) are generally present in a mixed or combined state with heterogeneous components generated as unreacted raw materials in each reaction step, as side reactions or reaction with water, or as natural decomposition of the compounds. A trace amount of these components may remain to exist with the main components.

According to the embodiment, since attention is paid to these heterogeneous components mixed or combined with the main compounds, even a trace amount of the heterogeneous components is treated as a composition mixed or combined with the main compounds to specifically illustrate the components and contents thereof.

In addition, in the present specification, for clear and easy distinction between various compositions, terms are also described in combination with the names of the main components in the composition. For example, a "diamine hydrochloride composition" refers to a composition comprising a diamine hydrochloride as a main component, and a "diisocyanate composition" refers to a composition comprising a diisocyanate as a main component. In such event, the content of the main component in the composition may be 50% by weight or more, 80% by weight or more, or 90% by weight or more, for example, 90% by weight to 99.9% by weight.

In this specification, the unit of ppm is by weight.

[Diisocyanate Composition]

The diisocyanate composition according to an embodiment comprises a diisocyanate; and a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof.

First, if an optical material is prepared while the content of a benzyl isocyanate having a methyl group in the diisocyanate composition is adjusted to the optimum range, it is possible to further enhance the physical properties of the optical material.

According to an embodiment of the present invention, the benzyl isocyanate having a methyl group may be intentionally added to the diisocyanate composition.

In addition, the benzyl isocyanate having a methyl group may be produced during the process for preparing the diisocyanate composition.

In addition, the benzyl isocyanate having a methyl group may be produced during the process for preparing the diisocyanate composition, and a part thereof may be intentionally added. That is, the benzyl isocyanate having a methyl group may be produced during the process for preparing the diisocyanate composition. If the amount thus produced is not sufficient, it may be intentionally added to the composition such that the content thereof is 5 ppm to 200 ppm in the composition.

The benzyl isocyanate having a methyl group may comprise a benzyl isocyanate having a methyl group with a specific aromatic structure. Specifically, it may comprise at least one selected from the group consisting of 2-methyl-benzyl isocyanate substituted with a methyl group at the ortho (o) position, 3-methylbenzyl isocyanate substituted with a methyl group at the meta (m) position, and 4-methylbenzyl isocyanate substituted with a methyl group at the para (p) position.

According to an embodiment of the present invention, the benzyl isocyanate having a methyl group may comprise at least one selected from the group consisting of 3-methylbenzyl isocyanate substituted with a methyl group at the meta (m) position and 4-methylbenzyl isocyanate substituted with a methyl group at the para (p) position.

According to an embodiment of the present invention, a benzyl isocyanate having a methyl group, in particular, 3-methylbenzyl isocyanate or 4-methylbenzyl isocyanate is employed in a specific amount. In such event, since it has one isocyanate functional group, it may stop the crosslinking reaction in the reaction for producing a polythiourethane, thereby promoting the enhancement in the flexibility of the polythiourethane. Thus, it is possible to prevent the occurrence of striae and cloudiness in an optical material, for example, an optical lens and enhancing the impact resistance at the same time.

More specifically, the benzyl isocyanate having a methyl group may comprise a compound of the following Formula 1 in which a methyl group is substituted at the meta (m) position.

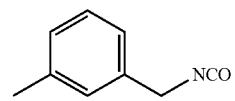

[Formula 1]

According to an embodiment of the present invention, the content of the benzyl isocyanate having a methyl group contained in the composition may be 5 ppm to 200 ppm, 10 ppm to 200 ppm, 20 ppm to 150 ppm, 20 ppm to less than 100 ppm, 100 ppm to 200 ppm, 120 ppm to 200 ppm, 50 ppm to 200 ppm, or 50 ppm to 150 ppm. According to an embodiment of the present invention, the content of the benzyl isocyanate having a methyl group contained in the composition is adjusted within the above range, whereby it is possible to enhance the impact resistance and to prevent the occurrence of striae and cloudiness.

If the content of the benzyl isocyanate having a methyl group is not adjusted, the impact resistance may be deteriorated, or striae and cloudiness may occur even if the impact resistance is maintained. For example, if the content of the benzyl isocyanate having a methyl group is less than 5 ppm, the impact resistance of the optical material using the composition may be deteriorated. On the other hand, if the content of the benzyl isocyanate having a methyl group exceeds 200 ppm, striae or cloudiness may occur even if the impact resistance of the optical material using the composition is enhanced.

In addition, if an optical material is prepared while the content of the aromatic compound having a halogen group in the diisocyanate composition is adjusted to the optimum range, it is possible to improve the physical properties of the optical material by preventing the occurrence of striae and cloudiness and lowering the yellow index and to enhance the impact resistance at the same time.

According to an embodiment of the present invention, the aromatic compound having a halogen group may be intentionally added to the diisocyanate composition.

In addition, the aromatic compound having a halogen group may be produced during the process for preparing the diisocyanate composition.

In addition, the aromatic compound having a halogen group may be produced during the process for preparing the diisocyanate composition, and a part thereof may be intentionally added. That is, the aromatic compound having a halogen group may be produced during the process for preparing the diisocyanate composition. If the amount thus produced is not sufficient, it may be intentionally added to the composition such that the content thereof is 5 ppm to 1,000 ppm.

In the aromatic compound having a halogen group, the aromatic compound may contain two or more halogen groups. In addition, the halogen may comprise chlorine.

Specifically, the aromatic compound having a halogen group may comprise a compound of the following Formula 2.

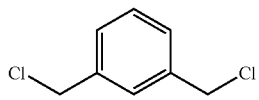

[Formula 2]

According to an embodiment, the content of the aromatic compound having a halogen group contained in the composition may be 5 ppm to 1,000 ppm, 5 ppm to 750 ppm, 10 ppm to 700 ppm, 10 ppm to 500 ppm, 20 ppm to 500 ppm, 20 ppm to 350 ppm, 150 ppm to 500 ppm, 500 ppm to 750 ppm, 750 ppm to 900 ppm, or 20 ppm to 150 ppm. According to an embodiment of the present invention, the content of the aromatic compound having a halogen group contained in the composition is adjusted within the above range, whereby it is possible to enhance the impact resistance and to prevent the occurrence of striae and cloudiness and lower the yellow index.

If the content of the aromatic compound having a halogen group is not adjusted, the impact resistance may be deteriorated, or striae and cloudiness may occur and the yellow index may be increased even if the impact resistance is maintained. For example, if the content of the aromatic compound having a halogen group is less than 5 ppm, the impact resistance of the optical material using the composition may be deteriorated. On the other hand, if the content of the aromatic compound having a halogen group exceeds 1,000 ppm, striae or cloudiness may occur and the yellow index may be increased even if the impact resistance of the optical material using the composition is enhanced.

In addition, the content of a benzyl isocyanate having an ethyl group in the diisocyanate composition used for the preparation of a polythiourethane-based optical material is adjusted, whereby it is possible to improve the optical characteristics of the optical material by preventing the occurrence of yellowing, striae, and cloudiness and by increasing the transmittance and to enhance the mechanical properties at the same time.

If the content of the benzyl isocyanate having an ethyl group is excessive, it may have an adverse impact on the optical characteristics and mechanical characteristics when the composition is applied to an optical material. In particular, the benzyl isocyanate having an ethyl group may precipitate as a solid when the concentration exceeds a certain level due to its low solubility, resulting in the occurrence of cloudiness, a decrease in the transmittance, and an increase in the yellow index.

The benzyl isocyanate having an ethyl group may comprise a benzyl isocyanate having an ethyl group with a specific aromatic structure. Specifically, it may comprise at least one selected from the group consisting of 1-ethyl-2-(isocyanatomethyl)benzene substituted with an ethyl group at the ortho (o) position, 1-ethyl-3-(isocyanatomethyl)benzene substituted with an ethyl group at the meta (m) position, and 1-ethyl-4-(isocyanatomethyl)benzene substituted with an ethyl group at the para (p) position.

According to an embodiment of the present invention, the benzyl isocyanate having an ethyl group may comprise at least one selected from the group consisting of 1-ethyl-3-(isocyanatomethyl)benzene and 1-ethyl-4-(isocyanatomethyl)benzene. According to an embodiment of the present invention, if the content of the benzyl isocyanate having an ethyl group, in particular, 1-ethyl-3-(isocyanatomethyl)benzene and/or 1-ethyl-4-(isocyanatomethyl)benzene is adjusted within a specific range, it is possible to prevent the material having a low solubility from being precipitated as a solid, thereby preventing the occurrence of striae and cloudiness in an optical material, for example, an optical lens, and enhancing the transmittance.

More specifically, the benzyl isocyanate having an ethyl group may comprise a compound of the following Formula 3 in which an ethyl group is substituted at the meta (m) position.

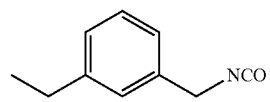

[Formula 3]

According to an embodiment of the present invention, the content of the benzyl isocyanate having an ethyl group contained in the composition may be 1 ppm to 1,000 ppm, 1 ppm to 800 ppm, 1 ppm to 700 ppm, 1 ppm to 500 ppm, 1 ppm to 350 ppm, 1 ppm to 300 ppm, 1 ppm to 250 ppm, 1 ppm to 200 ppm, 1 ppm to 150 ppm, 1 ppm to 100 ppm, 1 ppm to 50 ppm, or 10 ppm to 350 ppm. According to an embodiment of the present invention, the content of the benzyl isocyanate having an ethyl group, in particular, the compound of the above Formula 3, contained in the composition is adjusted within the above range, whereby it is possible to prevent the occurrence of striae and cloudiness, to lower the yellow index, and to enhance the transmittance.

If the content of the benzyl isocyanate having an ethyl group is not adjusted, cloudiness may occur, and the transmittance may be deteriorated. Further, if the content of the benzyl isocyanate having an ethyl group is excessive, the purity or yield of a crude product, for example, the reaction product (before distillation) of a diamine hydrochloride composition and triphosgene may be deteriorated. If the content of the benzyl isocyanate having an ethyl group exceeds 1,000 ppm, cloudiness may occur in the optical material using the composition, and the transmittance may be deteriorated. In addition, even if there is no problem in the optical characteristics, the purity or yield of the diisocyanate composition, which is a reaction product of a diamine hydrochloride composition and triphosgene, may be decreased.

Meanwhile, the diisocyanate composition may comprise 99.9% by weight to less than 100% by weight of a diisocyanate based on the total weight of the composition.

The diisocyanate may comprise m-xylylene diisocyanate (m-XDI), p-xylylene diisocyanate (p-XDI), or a mixture thereof.

The diisocyanate composition according to an embodiment may comprise m-xylylene diisocyanate (m-XDI) in an amount of 99% by weight to less than 100% by weight, for example, 99.5% by weight to less than 100% by weight or 99.7% by weight to less than 100% by weight.

If m-xylylene diisocyanate is contained in the composition in an amount less than the above range, not only the optical characteristics (especially, striae, transmittance, and the like) but also the mechanical properties (such as impact resistance, tensile strength, and the like) of the final product may be impaired due to the nonuniformity in the polymerization reactivity of the composition and in the chemical structure of the cured product. Further, yellowing may occur depending on other components incorporated therein.

According to an embodiment, the composition may comprise the compound of Formula 1 in an amount of 20 ppm to 150 ppm and m-xylylene diisocyanate in an amount of 99.5% by weight to less than 100% by weight based on the total weight of the composition.

According to another embodiment, the composition may comprise the aromatic compound having a halogen group in an amount of 20 ppm to 500 ppm and m-xylylene diisocyanate in an amount of 99.5% by weight to less than 100% by weight based on the total weight of the composition.

According to still another embodiment, the composition may comprise the benzyl isocyanate having an ethyl group, in particular, the compound of Formula 1, in an amount of 1 ppm to 500 ppm, specifically 10 ppm to 350 ppm and m-xylylene diisocyanate in an amount of 99.5% by weight to less than 100% by weight based on the total weight of the composition.

In addition, the composition may comprise p-xylylene diisocyanate in an amount of greater than 0% by weight to 0.5% by weight, greater than 0% by weight to 0.3% by weight, greater than 0% by weight to 0.15% by weight, greater than 0% by weight to 0.1% by weight, greater than 0% by weight to 0.05% by weight, greater than 0% by weight to 0.03% by weight, or greater than 0% by weight to 0.01% by weight, based on the total weight of the composition.

If p-xylylene diisocyanate is contained in the composition in an amount exceeding the above content range, the optical characteristics may be impaired as striae occur or the transmittance is lowered due to the nonuniform polymerization caused by differences in the reactivity or due to the crystallization caused by changes in the chemical structure of the polymer.

The diisocyanate composition may comprise other diisocyanates used in the preparation of optical lenses than m-xylylene diisocyanate and p-xylylene diisocyanate. Specifically, the composition may further comprise at least one selected from the group consisting of orthoxylylene diisocyanate (o-XDI), norbornene diisocyanate (NBDI), hydrogenated xylylene diisocyanate (H6XDI), isophorone diisocyanate (IPDI), and hexamethylene diisocyanate (HDI).

In addition, the diisocyanate composition may further comprise at least one selected from the group consisting of a benzyl isocyanate having an ethyl group and cyanobenzyl isocyanate while it comprises a benzyl isocyanate having a methyl group.

The at least one selected from the group consisting of a benzyl isocyanate having an ethyl group and cyanobenzyl isocyanate may be employed in an amount of, for example, 0.5% by weight or less, 0.3% by weight or less, 0.1% by weight or less, 0.05% by weight or less, 0.02% by weight or less, or 0.01% by weight or less.

If the at least one selected from the group consisting of a benzyl isocyanate having an ethyl group and cyanobenzyl isocyanate is employed in the composition in an amount exceeding the above content range, it affects the chemical structure of the polymer, resulting in a deterioration in the mechanical properties or the thermal resistant characteristics such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

In addition, the diisocyanate composition may further comprise at least one selected from the group consisting of methylbenzyl isocyanate and cyanobenzyl isocyanate while it comprises an aromatic compound having a halogen group. Specifically, the diisocyanate composition according to an embodiment of the present invention may further comprise at least one selected from the group consisting of 4-methylbenzylisocyanate and 4-cyanobenzylisocyanate while it comprises an aromatic compound having a halogen group.

The at least one selected from the group consisting of 4-methylbenzylisocyanate and 4-cyanobenzylisocyanate may be employed in an amount of, for example, 0.5% by weight or less, 0.3% by weight or less, 0.1% by weight or less, 0.05% by weight or less, 0.02% by weight or less, or 0.01% by weight or less.

If 4-methylbenzylisocyanate or 4-cyanobenzylisocyanate is employed in the composition in an amount exceeding the above content range, the equivalent ratios of the composition are changed due to a decrease in the average number of functional groups in the composition, which affects the chemical structure of the polymer, resulting in a deterioration in the mechanical properties or the thermal resistant characteristics such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

In addition, the diisocyanate composition may further comprise at least one selected from the group consisting of a benzyl isocyanate having a methyl group and cyanobenzyl isocyanate while it comprises a benzyl isocyanate having an ethyl group.

The at least one selected from the group consisting of a benzyl isocyanate having an methyl group and cyanobenzyl isocyanate may be employed in an amount of, for example, 0.5% by weight or less, 0.3% by weight or less, 0.1% by weight or less, 0.05% by weight or less, 0.02% by weight or less, or 0.01% by weight or less.

If the at least one selected from the group consisting of a benzyl isocyanate having a methyl group and cyanobenzyl isocyanate is employed in the composition in an amount exceeding the above content range, it affects the chemical structure of the polymer, resulting in a deterioration in the mechanical properties or the thermal resistant characteristics such as glass transition temperature of the final product. Further, due to the influence of the cyano groups, yellowing may occur at the time of thermal curing for producing a lens or after the production of the lens depending on the external environment, thereby causing serious damage to the long-term reliability of the lens.

Therefore, a product produced from the diisocyanate composition whose composition has been adjusted as described above can satisfy excellent optical characteristics, as well as can achieve excellent mechanical properties. Thus, it can be advantageously used for the production of optical materials, specifically plastic optical lenses.

[Process for Preparing a Diisocyanate Composition]

The process for preparing a diisocyanate composition according to another embodiment comprises obtaining a diamine hydrochloride composition; treating the diamine hydrochloride composition; and obtaining a diisocyanate composition using the treated diamine hydrochloride composition and triphosgene, wherein the content of a benzyl isocyanate having a methyl group is 5 ppm to 200 ppm, the content of an aromatic compound having a halogen group is 5 ppm to 1,000 ppm, or the content of a benzyl isocyanate having an ethyl group is 1 ppm to 1,000 ppm in the diisocyanate composition.

FIG. 1A and FIG. 1B schematically show the process for preparing a diisocyanate composition according to an embodiment. In FIG. 1A and FIG. 1B, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In FIG. 1A, (i) may comprise a step of adding an aqueous hydrochloric acid solution to react a diamine with the aqueous hydrochloric acid solution. In FIG. 1A, (ii) may comprise at least one step selected from a precipitation step, a filtration step, a drying step, and a washing step. In FIG. 1B, (iii) may comprise a step of adding triphosgene to react a diamine hydrochloride composition with triphosgene. In FIG. 1B, (iv) may comprise at least one step selected from a degassing step, a filtration step, and a distillation step.

According to an embodiment of the present invention, the content of the benzyl isocyanate having a methyl group may be adjusted by adding the benzyl isocyanate having a methyl group to the diisocyanate composition. For example, according to an embodiment of the present invention, the content of the benzyl isocyanate having a methyl group may be adjusted by introducing the benzyl isocyanate having a methyl group in the step of obtaining the diamine hydrochloride composition and/or the step of obtaining the diisocyanate composition.

In addition, the benzyl isocyanate having a methyl group may be produced during the process for preparing the diisocyanate composition. For example, it may be produced in the process for preparing a diisocyanate composition during the reaction in the step of obtaining the diamine hydrochloride composition and/or the step of obtaining the diisocyanate composition.

In addition, the benzyl isocyanate having a methyl group may be produced during the process for preparing the diisocyanate composition, and a part thereof may be further added. That is, the amount of the benzyl isocyanate having a methyl group produced during the process for preparing the diisocyanate composition is not sufficient, it may be further added to the composition such that the content thereof is 5 ppm to 200 ppm.

The content of the benzyl isocyanate having a methyl group contained in the composition is adjusted within the above range, whereby it is possible to enhance the impact resistance and to prevent the occurrence of striae and cloudiness at the same time when the composition is applied to an optical material.

In addition, according to an embodiment of the present invention, the content of the aromatic compound having a halogen group may be adjusted by adding the aromatic compound having a halogen group to the diisocyanate composition. For example, according to an embodiment of the present invention, the content of the aromatic compound having a halogen group may be adjusted by introducing the aromatic compound having a halogen group in the step of obtaining the diamine hydrochloride composition and/or the step of obtaining the diisocyanate composition.

In addition, the aromatic compound having a halogen group may be produced during the process for preparing the diisocyanate composition. For example, it may be produced in the process for preparing a diisocyanate composition during the reaction in the step of obtaining the diamine hydrochloride composition and/or the step of obtaining the diisocyanate composition.

In addition, the aromatic compound having a halogen group may be produced during the process for preparing the diisocyanate composition, and a part thereof may be further added. That is, the amount of the aromatic compound having a halogen group produced during the process for preparing the diisocyanate composition is not sufficient, it may be further added to the composition such that the content thereof is 5 ppm to 1,000 ppm.

The content of the aromatic compound having a halogen group contained in the composition is adjusted within the above range, whereby it is possible to enhance the impact resistance and to prevent the occurrence of striae and cloudiness at the same time when the composition is applied to an optical material.

In addition, in the process for preparing a diisocyanate composition according to an embodiment of the present invention, the content of the benzyl isocyanate having an ethyl group may be adjusted to 1 ppm to 1,000 ppm by the above process. In particular, when the treated diamine hydrochloride composition is reacted with triphosgene, the reaction temperature is controlled to a temperature of 110° C. to 130° C., whereby it is possible to efficiently adjust the content of the benzyl isocyanate having an ethyl group in a convenient way.

Further, an aqueous hydrochloric acid solution, without the use of hydrogen chloride gas, is used to prepare a diamine hydrochloride as an intermediate, so that the reaction can be carried out even at atmospheric pressure, and an additional apparatus for high-temperature heating and cooling is not required. Thus, it is possible to simultaneously enhance the purity and yield of the diisocyanate composition thus prepared and the final product of the optical material using the same.

Hereinafter, each step will be described in detail.

Preparation of a Diamine Hydrochloride Composition

The process for preparing a diisocyanate composition according to an embodiment of the present invention comprises obtaining a diamine hydrochloride composition.

The step of obtaining a diamine hydrochloride composition may comprise reacting a diamine with an aqueous hydrochloric acid solution. In addition, after the reaction of a diamine and an aqueous hydrochloric acid solution, a first organic solvent may be further added to obtain the diamine hydrochloride composition in a solid phase.

The following Reaction Scheme 1 shows an example of the reaction in this step.

[Reaction Scheme 1]

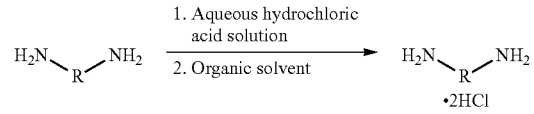

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

In the conventional method in which hydrogen chloride gas is used, a hydrochloride is produced as fine particles upon the reaction at atmospheric pressure, so that the agitation inside the reactor is not smoothly carried out. Thus, an additional process of raising the pressure to increase the internal temperature of the reactor is required, and there is a problem that the yield of the final product is low as well.

According to the above embodiment, however, since an aqueous hydrochloric acid solution is used, it is possible to solve the problem involved in the prior art in which hydrogen chloride gas is used. Specifically, when an aqueous hydrochloric acid solution is used, the product obtained through the reaction is in a solid form rather than a slurry form, so that the yield is high. The reaction can be carried out even at atmospheric pressure, so that a separate apparatus or process for rapid cooling is not required.

The concentration of the aqueous hydrochloric acid solution may be 5% by weight to 50% by weight. Within the above concentration range, it is possible to minimize the dissolution of the hydrochloride in the aqueous hydrochloric acid solution, thereby enhancing the final yield, and to improve the handling convenience.

Specifically, the concentration of the aqueous hydrochloric acid solution may be 10% by weight to 45% by weight, 20% by weight to 45% by weight, or 30% by weight to 40% by weight. More specifically, the aqueous hydrochloric acid solution may have a concentration of 20% by weight to 45% by weight.

The diamine and the aqueous hydrochloric acid solution may be introduced to the reaction at an equivalent ratio of 1:2 to 5. If the equivalent ratio is within the above range, it is possible to reduce the unreacted materials and to prevent a decrease in the yield caused by dissolution as water is generated. Specifically, the diamine and the aqueous hydrochloric acid solution may be introduced to the reaction at an equivalent ratio of 1:2 to 2.5.

The introduction of the diamine and the aqueous hydrochloric acid solution may be carried out while the internal temperature of the reactor is maintained to be constant.

When the diamine and the aqueous hydrochloric acid solution are introduced, the internal temperature of the reactor may be in a range of 20° C. to 100° C. Within the above temperature range, it is possible to prevent the temperature from being raised above the boiling point, which is not suitable for the reaction, or the temperature from being lowered too much, whereby the reaction efficiency is reduced.

Specifically, when the diamine and the aqueous hydrochloric acid solution are introduced, the internal temperature of the reactor may be 20° C. to 60° C., 20° C. to less than 60° C., 20° C. to 50° C., or 20° C. to 40° C.

More specifically, the diamine and the aqueous hydrochloric acid solution may be introduced to the reaction at an equivalent ratio of 1:2 to 5 at a temperature of 20° C. to 60° C.

In the conventional hydrochloride method, a large amount of heat is generated in the reaction, which requires rapid cooling through a separate cooler, whereas the reaction materials are introduced while a low temperature is maintained according to the above embodiment, which does not require a separate cooler.

The introduction of the diamine and the aqueous hydrochloric acid solution may be carried out, for example, in a sequence in which the aqueous hydrochloric acid solution may be first introduced to the reactor and the diamine may then be slowly introduced to the reactor. The introduction of the diamine and/or the aqueous hydrochloric acid solution may be carried out for 30 minutes to 1 hour.

When the introduction of the diamine and the aqueous hydrochloric acid solution is completed, the internal temperature of the reactor may be lowered to 0° C. to 20° C., 0° C. to 10° C., or 10° C. to 20° C.

The reaction between the diamine and the aqueous hydrochloric acid solution may be carried out at atmospheric pressure for, for example, 30 minutes to 2 hours with stirring.

As a result of the reaction between the diamine and the aqueous hydrochloric acid solution, a diamine hydrochloride composition in an aqueous solution form may be obtained as the reaction resultant.

Treatment of a Diamine Hydrochloride Composition

According to an embodiment of the present invention, the process may further comprise treating the diamine hydrochloride composition after the diamine hydrochloride composition is obtained.

For example, the step of treating the diamine hydrochloride composition may comprise at least one of precipitating the diamine hydrochloride composition, filtering the diamine hydrochloride composition, drying the diamine hydrochloride composition, and washing the diamine hydrochloride composition.

Specifically, a first organic solvent may be introduced to the reaction resultant to precipitate a solid diamine hydrochloride composition. That is, the first organic solvent may induce the precipitation of a solid diamine hydrochloride composition through crystallization. More specifically, the first organic solvent may be introduced to the reaction resultant, which is cooled and further stirred to carry out the reaction.

The first organic solvent may be at least one selected from the group consisting of diethyl ether, diisopropyl ether, dioxane, tetrahydrofuran, methanol, ethanol, dimethyl sulfoxide, dimethylformamide, acetonitrile, acetone, trichloroethylene, tetrachloroethane, trichloroethanol, n-butanol, isobutanol, methyl ethyl ketone, methyl butyl ketone, isopropanol, hexane, chloroform, and methyl acetate.

The amount (weight) of the first organic solvent introduced may be 1 to 5 times the weight of the diamine. If the introduced amount is within the above range, it is possible to prevent the use of excessive organic solvents while the yield of the final hydrochloride is high. Specifically, the first organic solvent may be introduced to the reaction in an amount of 1 to 2 times, or 1 to 1.5 times, the weight of the diamine.

After the first organic solvent is introduced, the cooling temperature may be −10° C. to 10° C. or −5° C. to 5° C. In addition, the additional reaction time after the cooling may be 30 minutes to 2 hours or 30 minutes to 1 hour.

According to a specific example, the steps of (1a) introducing the aqueous hydrochloric acid solution to a first reactor; (1b) introducing the diamine to the first reactor and stirring them; and (1c) introducing the first organic solvent to the first reactor and stirring them may be sequentially carried out.

More specifically, the process may further comprise cooling the inside of the reactor to a temperature of 0° C. to 10° C. after the introduction of the diamine and before stirring in step (1b); and cooling the inside of the reactor to a temperature of −5° C. to 5° C. after the introduction of the first organic solvent and before stirring in step (1c).

After the first organic solvent is introduced, separation, filtration, washing, and drying may be further carried out. For example, after the first organic solvent is introduced, the aqueous layer may be separated, filtered, washed, and dried to obtain a solid diamine hydrochloride composition. The washing may be carried out one or more times using, for example, a solvent having a polarity index of 5.7 or less. In addition, the drying may be carried out using vacuum drying. For example, it may be carried out at a temperature of 40° C. to 90° C. and a pressure of 2.0 torr or less.

As a result, the impurities generated in the step of obtaining the diamine hydrochloride composition may be removed together with the first organic solvent. Thus, the process may further comprise removing the impurities generated in the step of obtaining the diamine hydrochloride composition together with the first organic solvent. Impurities are generated in the reaction for preparing the diamine hydrochloride composition and are contained in the first organic solvent. Such impurities may be removed by the step of removing the first organic solvent, whereby the purity of the product may be increased.

According to the above process, a diamine is reacted with an aqueous hydrochloric acid solution, which is then subjected to additional treatment such as precipitation, filtration, drying, and washing, whereby a solid diamine hydrochloride composition can be obtained with high purity. In contrast, in the conventional process in which a diamine is reacted with hydrogen chloride gas in an organic solvent, a slurry of a diamine hydrochloride is obtained, which is not readily purified.

The yield of the diamine hydrochloride composition thus obtained may be 50% or more, 65% or more, 80% or more, 85% or more, or 90% or more, specifically 85% to 95% or 88% to 92%.

Meanwhile, the organic layer can be separated from the reactant and recycled as an organic solvent. Thus, the recovery rate of the first organic solvent may be 80% or more, 85% or more, or 90% or more, specifically 80% to 95% or 80% to 82%.

Preparation of a Diisocyanate Composition

The diamine hydrochloride composition is reacted with triphosgene to obtain a diisocyanate composition.

The step of obtaining a diisocyanate composition may comprise reacting the diamine hydrochloride composition, treated by the process comprising at least one of precipitation, filtration, drying, and/or washing, with triphosgene.

In such event, the reaction of the diamine hydrochloride composition with triphosgene may be carried out in a second organic solvent.

The following Reaction Scheme 2 shows an example of the reaction in this step.

[Reaction Scheme 2]

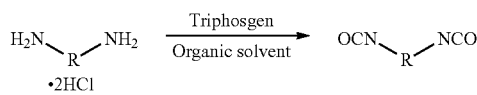

In the above scheme, R comprises an aromatic ring, an aliphatic ring, an aliphatic chain, and the like. As a specific example, R may be xylylene, norbornene, hydrogenated xylylene, isophorone, or hexamethylene, but it is not limited thereto.

Specifically, the diamine hydrochloride composition prepared above is introduced to a second organic solvent, reacted with triphosgene (BTMC, bis(trichloromethyl)carbonate), and then purified to obtain a diisocyanate composition.

Specifically, the second organic solvent may be at least one selected from the group consisting of benzene, toluene, ethylbenzene, chlorobenzene, monochlorobenzene, 1,2-dichlorobenzene (ODCB), dichloromethane, 1-chloro-n-butane, 1-chloro-n-pentane, 1-chloro-n-hexane, chloroform, carbon tetrachloride, n-pentane, n-hexane, n-heptane, n-octane, cyclohexane, cyclopentane, cyclooctane, and methylcyclohexane.

The amount (weight) of the second organic solvent introduced may be 1 to 5 times the weight of the diamine hydrochloride composition. If the introduced amount is within the above range, it is possible to prevent the use of excessive organic solvents while the yield of the final diisocyanate is high. Specifically, the second organic solvent may be introduced to the reaction in an amount of 2 to 5 times, or 3 to 5 times, the weight of the diamine hydrochloride composition.

The reaction temperature of the diamine hydrochloride composition and triphosgene may be 110° C. to 160° C. or 110° C. to 130° C. If the reaction temperature is within the above range, the reaction between the diamine hydrochloride and triphosgene can be smoothly carried out, and it is possible to suppress the generation of impurities such as tar when the final diisocyanate is produced. Specifically, the reaction temperature of the diamine hydrochloride composition and triphosgene may be 115° C. to 160° C., 115° C. to 140° C., 115° C. to less than 130° C., 130° C. to 160° C., 120° C. to 150° C., 110° C. to 130° C., 110° C. to less than 130° C., 110° C. to 125° C., 110° C. to less than 120° C., or 120° C. to 130° C.

According to an embodiment of the present invention, if the content of the benzyl isocyanate having an ethyl group, in particular, the compound of Formula 3, is high, it causes cloudiness and low transmittance. The compound may be more produced in a reaction (e.g., a phosgenation reaction) under high-temperature conditions. Thus, the control of the reaction temperature to the above range may be very important. If the reaction temperature is less than 110° C. when the diamine hydrochloride composition is reacted with triphosgene, the reaction between the diamine hydrochloride composition and triphosgene may not be smoothly carried out, thereby lowering the yield. In addition, if the reaction temperature exceeds 130° C., the content of the benzyl isocyanate having an ethyl group in the diisocyanate composition may be increased, thereby deteriorating the optical characteristics of the optical material.

According to an embodiment of the present invention, if the reaction between the diamine hydrochloride composition and triphosgene is carried out within the range of 110° C. to 130° C., the content of the benzyl isocyanate having an ethyl group may be effectively adjusted to 1 ppm to 1,000 ppm, thereby enhancing the yield and purity. In addition, if the content of the benzyl isocyanate having an ethyl group, in particular, 1-ethyl-3-(isocyanatomethyl)benzene, in the diisocyanate composition is adjusted within the above range, the transmittance is excellent, and it is possible to reduce the occurrence of yellowing, striae, and cloudiness. In addition, an appropriate level of refractive index can be achieved. Thus, when the composition is applied to an optical material, the optical material may have high quality with excellent optical characteristics as well as excellent mechanical properties.

The reaction of the diamine hydrochloride composition with triphosgene may be carried out for 5 hours to 100 hours. If the reaction time is within the above range, the reaction time is not excessive, and the production of unreacted materials due to the generation of phosgene can be minimized. Specifically, the reaction of the diamine hydrochloride composition with triphosgene may be carried out for 15 hours to 40 hours, hours to 35 hours, or 24 hours to 30 hours.

As a specific example, the reaction of the diamine hydrochloride composition with triphosgene may be carried out at a temperature of 110° C. to 160° C. for 5 hours to 100 hours.

The diamine hydrochloride composition and triphosgene may be introduced to the reaction at an equivalent ratio of 1:1 to 5. When the equivalent ratio is within the above range, the reaction efficiency is high, and it is possible to prevent an increase in the reaction time due to an excessive introduction. Specifically, the diamine hydrochloride composition and triphosgene may be introduced to the reaction at an equivalent ratio of 1:1.5 to 4 or 1:2 to 2.5.

The reaction of the diamine hydrochloride composition and triphosgene may sequentially comprise mixing the diamine hydrochloride composition with a second organic solvent to obtain a first solution; mixing triphosgene with a second organic solvent to obtain a second solution; and introducing the second solution to the first solution and stirring them. In such event, the introduction of the second solution and stirring may be carried out at a temperature of 110° C. to 160° C. or 110° C. to 130° C. In addition, the introduction of the second solution may be divided into two or more times for a total of 25 hours to 40 hours. In addition, here, the time for each introduction may be 5 hours to 25 hours or 10 hours to 14 hours. In addition, the time for further reaction by stirring after the introduction may be 2 hours to 5 hours or 3 hours to 4 hours.

According to a specific example, the reaction of the diamine hydrochloride composition and triphosgene may sequentially comprise (2a) introducing the second organic solvent to a second reactor; (2b) further introducing the diamine hydrochloride composition to the second reactor and stirring them; and (2c) further introducing triphosgene to the second reactor and stirring them.

More specifically, the introduction of triphosgene in step (2c) may be carried out by introducing a solution in which triphosgene is dissolved in the same solvent as the second organic solvent to the reactor as divided into two or more times at a temperature of 110° C. to 160° C. or 110° C. to 130° C. for a total of 25 hours to 40 hours.

In such event, the time for each introduction of triphosgene may be 5 hours to 25 hours or 10 hours to 14 hours.

In addition, the time for further reaction by stirring after the introduction of triphosgene may be 2 hours to 5 hours or 3 hours to 4 hours.

Upon the reaction, the reactant may be cooled at a temperature of 90° C. to 110° C.

The reaction resultant obtained through the reaction may be further subjected to separation, filtration, and distillation.

The distillation may comprise first distillation and second distillation.

For example, the step of obtaining the diisocyanate composition further comprises distilling the reaction resultant obtained by reacting the diamine hydrochloride composition, specifically the treated diamine hydrochloride composition, and triphosgene. The distillation may comprise first distillation at 40° C. to 60° C. for 2 hours to 8 hours and second distillation at 100° C. to 120° C. for 2 hours to 10 hours. The first distillation and/or the second distillation may be carried out at 0.5 Torr or less.

The organic solvent may be recovered and recycled through the first distillation, and a final diisocyanate may be obtained through the second distillation.

In addition, the yield of the (crude) diisocyanate composition before distillation may be 80% or more, 85% or more, or 90% or more.

In addition, the yield of the diisocyanate composition obtained after distillation may be 80% or more, 85% or more, 90% or more, 95% or more, 98% or more, or 99% or more.

According to an embodiment of the present invention, the content of the benzyl isocyanate having a methyl group contained in the composition may be adjusted by introducing the benzyl isocyanate having a methyl group in the step of obtaining the diamine hydrochloride composition, the step of obtaining the diisocyanate composition, and after the first distillation or after the second distillation in the step of obtaining the diisocyanate composition. Alternatively, the content of the benzyl isocyanate having a methyl group may be adjusted by introducing the benzyl isocyanate having a methyl group before the diisocyanate composition is mixed with a thiol or an episulfide in the process of preparing an optical material. Alternatively, the content of the benzyl isocyanate having a methyl group may be adjusted by introducing it as divided in the above timings of addition. Alternatively, the benzyl isocyanate having a methyl group may be produced during at least one step of the above process.

Measurement of the Color and Transparency of a Reaction Solution

The step of obtaining a diisocyanate composition from the diamine hydrochloride composition and triphosgene may comprise (aa) reacting the diamine hydrochloride composition with triphosgene in a reactor to obtain a reaction solution; (ab) measuring the color and transparency of the reaction solution; and (ac) obtaining a diisocyanate composition from the reaction solution.

In the reaction of the diamine hydrochloride composition and triphosgene, the color and transparency of the reaction solution may be measured to adjust the reaction conditions.

For example, in the reaction of metaxylylenediamine hydrochloride and triphosgene to obtain metaxylylene diisocyanate, the reaction solution at the beginning of the reaction may be opaque colorless or white, and the reaction solution at the time when the reaction is ordinarily completed may be transparent or close to transparent in a light brown color.

For example, in the step of measuring the color and transparency of the reaction solution, the reaction solution may have a transparent light brown color.

Specifically, the reaction solution may have an $L^*$ value of 45 to 60, an $a^*$ value of 3 to 15, and a $b^*$ value of 15 to 30 in the CIE-LAB color coordinate. More specifically, the reaction solution may have an $L^*$ value of 50 to 55, an $a^*$ value of 5 to 10, and a $b^*$ value of 20 to 25 in the CIE-LAB color coordinate.

In addition, the reaction solution may have a transmittance of 60% or more, 70% or more, 80% or more, or 90% or more, for light having a wavelength of 550 nm. In addition, the reaction solution may have a haze of 20% or less, 10% or less, 5% or less, or 3% or less. Specifically, the reaction solution may have a transmittance of 70% or more for light having a wavelength of 550 nm and a haze of 10% or less. More specifically, the reaction solution may have a transmittance of 80% or more for light having a wavelength of 550 nm and a haze of 5% or less.

On the other hand, if the reaction of the metaxylylenediamine hydrochloride composition and triphosgene is not completed, the reaction solution may be opaque or have a precipitate, and the color may be pale, white, or colorless. In addition, if side reactions take place to a significant extent, the reaction solution may be opaque or may have a color other than light brown, for example, a dark brown or dark color.

The reaction of the diamine hydrochloride composition and triphosgene may be carried out simultaneously with the step of measuring the color and transparency of the reaction solution.

That is, while the reaction of the diamine hydrochloride composition and triphosgene is being carried out, the color and transparency of the reaction solution may be measured in real time.

In addition, for more accurate measurement, a part of the reaction solution may be collected to precisely measure the color and transparency thereof. For example, the measurement of the color and transparency of the reaction solution may be carried out by collecting a part of the reaction solution and measuring the color and transparency of the collected reaction solution.

In such event, the reaction equivalent, reaction temperature, or reaction time may be adjusted according to the color and transparency of the reaction solution. For example, the timing for terminating the reaction may be determined according to the color and transparency of the reaction solution. Specifically, the timing for terminating the reaction may come after when the reaction solution turns a transparent light brown color.

As an example, the reactor may have a viewing window, and the measurement of the color and transparency of the reaction solution may be carried out through the viewing window.

The reactor is connected to one or more stages of condensers. Once the gas generated in the reactor has been transferred to the one or more stages of condensers, the second organic solvent present in the gas may be condensed and recycled to the reactor.

The one or more stages of condensers are connected to a first scrubber and a second scrubber. The gas transferred from the reactor to the one or more stages of condensers contains hydrogen chloride gas and phosgene gas, the first scrubber may dissolve the hydrogen chloride gas in water to produce an aqueous solution, and the second scrubber may neutralize the phosgene gas with an aqueous NaOH solution.

In addition, the reactor is connected to one or more stages of distillers. The reaction solution is transferred to the one or more stages of distillers, and the one or more stages of distillers may separate the diisocyanate composition and the second organic solvent from the reaction solution.

The separated second organic solvent may be recycled for the reaction of the diamine hydrochloride composition and triphosgene.

FIG. 2 shows an example of the process equipment for the reaction of a diamine hydrochloride composition and triphosgene.

First, a first tank (T-1) is charged with a second organic solvent and triphosgene, and the temperature is maintained to be constant by refluxing hot water. The inside of a reactor (R-1) is purged with nitrogen, a second organic solvent is introduced thereto with stirring, a diamine hydrochloride composition is slowly introduced thereto, and they are stirred while the internal temperature of the reactor is maintained to be constant.

Thereafter, triphosgene in the second organic solvent is gradually introduced into the reactor (R-1) from the first tank (T-1). The introduction of triphosgene in the second organic solvent is carried out at a time or divided into two or more times. At that time, stirring is performed while the internal temperature of the reactor (R-1) is maintained to be constant. Upon completion of the introduction, an additional reaction is carried out while stirring is performed for a certain period of time. As an example, the color and transparency of the reaction solution are monitored with the naked eyes through a viewing window (G-1) provided in the reactor (R-1). As another example, the color and transparency of the reaction solution are measured with an optical device through the viewing window (G-1) provided in the reactor (R-1). The optical device may include a digital camera, a spectrometer, and optical analysis equipment.

The gas (second organic solvent, hydrogen chloride, phosgene, and the like) present inside the reactor (R-1) is transferred to a first condenser (C-1). In the first condenser (C-1), the second organic solvent is firstly condensed by cooling and recycled to the reactor (R-1), and the remaining gas is transferred to a second condenser (C-2). In the second condenser (C-2), the second organic solvent is secondly condensed by cooling and recycled to the reactor (R-1), and the remaining gas is transferred to a third condenser (C-3). In the third condenser (C-3), the second organic solvent is thirdly condensed by cooling and recycled to the reactor (R-1).

Once the second organic solvent is removed while it passes through the multi-stage condensers as described above, the remaining gas (hydrogen chloride, phosgene, and the like) is transferred to a first scrubber (S-1). In the first scrubber (S-1), hydrogen chloride gas is dissolved in water to obtain an aqueous hydrochloric acid solution and stored in a second tank (T-2), and the remaining gas is transferred to a second scrubber (S-2). In the second scrubber (S-1), phosgene ($COCl_2$) gas may be neutralized with an aqueous sodium hydroxide solution stored in a third tank (T-3) and removed.

The reaction solution obtained from the reactor (R-1) is sequentially transferred to a first distiller (D-1) and a second distiller (D-2). While it undergoes first and second distillation, the diisocyanate composition and the second organic solvent are separated from the reaction solution.

The second organic solvent separated from the reaction solution may be transferred to, and stored in, a solvent recovery apparatus (V-1). Thereafter, it may be recycled for the reaction of the diamine hydrochloride composition and triphosgene.

In addition, the diisocyanate composition separated from the reaction solution may be further subjected to filtration and drying to provide a final product.

[Process for the Preparation of an Optical Material]

The diisocyanate prepared in the above embodiment may be combined with other components to prepare a polymerizable composition for an optical material.

The polymerizable composition for an optical material comprises a diisocyanate; and a benzyl isocyanate having a methyl group in an amount of 5 ppm to 200 ppm, an aromatic compound having a halogen group in an amount of 5 ppm to 1,000 ppm, a benzyl isocyanate having an ethyl group in an amount of 1 ppm to 1,000 ppm, or a combination thereof.

The polymerizable composition for an optical material further comprises a thiol or an episulfide.

The polymerizable composition for an optical material may be used to prepare an optical material, specifically an optical lens. For example, the polymerizable composition for an optical material is mixed and heated and cured in a mold to produce an optical lens.

The process for preparing an optical material according to an embodiment comprises reacting a diamine with an aqueous hydrochloric acid solution to obtain a diamine hydrochloride composition as a first step; reacting the diamine hydrochloride composition with triphosgene at a temperature of 110° C. to 160° C. or 110° C. to 130° C. to obtain a diisocyanate composition as a second step; and mixing the diisocyanate composition with a thiol or an episulfide and polymerizing and curing the resultant in a mold as a third step, wherein the content of a benzyl isocyanate having a methyl group is 5 ppm to 200 ppm, the content of an aromatic compound having a halogen group is 5 ppm to 1,000 ppm, or the content of a benzyl isocyanate having an ethyl group is 1 ppm to 1,000 ppm in the diisocyanate composition.

The content of the benzyl isocyanate having a methyl group may be adjusted by introducing the benzyl isocyanate having a methyl group in the reaction of the first step, in the reaction of the second step, after the first distillation or after the second distillation in the second step, or before the diisocyanate composition is mixed with a thiol or an episulfide in the third step.

In addition, the content of the aromatic compound having a halogen group may be adjusted by introducing the aromatic compound having a halogen group in the reaction of the first step, in the reaction of the second step, after the first distillation or after the second distillation in the second step, or before the diisocyanate composition is mixed with a thiol or an episulfide in the third step.

In addition, the diamine is xylylenediamine, and the diisocyanate composition may comprise xylylene diisocyanate.

The thiol may be a polythiol containing two or more SH groups. It may have an aliphatic, alicyclic, or aromatic skeleton. The episulfide may have two or more thioepoxy groups. It may have an aliphatic, alicyclic, or aromatic skeleton.

Specific examples of the thiol include bis(2-mercaptoethyl) sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis (mercaptomethyl)methane, 2-(2-mercaptoethylthio) propane-1,3-dithiol, 2-(2,3-bis(2-mercaptoethylthio) propylthio)ethanethiol, bis(2,3-dimercaptopropanyl)sulfide, bis(2,3-dimercaptopropanyl) disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl) sulfide, bis(2-(2-mercaptoethylthio)-3-mercaptopropyl) disulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol, (S)-3-((R-3-mercapto-2-((2-mercaptoethyl)thio)propyl)thio)-2-((2-mercaptoethyl)thio)propane-1-thiol, 3,3'-dithiobis(propane-1,2-dithiol), (7R,11 S)-7,11-bis (mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1, 11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaethritol tetrakis (2-mercaptoacetate), bispentaerythritol-ether-hexakis(3-mercaptopropionate), 1,1,3,3-tetrakis(mercaptomethylthio) propane, 1,1,2,2-tetrakis(mercaptomethylthio)ethane, 4,6-bis(mercaptomethylthio)-1,3-dithiane, 2-(2,2-bis (mercaptodimethylthio)ethyl)-1,3-dithiane, 2,5-bismercaptomethyl-1,4-dithiane, bis(mercaptomethyl)-3,6, 9-trithiaundecan-1,11-dithiol.

For example, the thiol may be 2-(2-mercaptoethylthio) propane-1,3-dithiol, 2,3-bis(2-mercaptoethylthio)propane-1-thiol, 2-(2,3-bis(2-mercaptoethylthio)propylthio)ethanethiol, 1,2-bis(2-mercaptoethylthio)-3-mercaptopropane, 1,2-bis(2-(2-mercaptoethylthio)-3-mercaptopropylthio)-ethane, bis(2-(2-mercaptoethylthio)-3-mercaptopropyl) sulfide, 2-(2-mercaptoethylthio)-3-2-mercapto-3-[3-mercapto-2-(2-mercaptoethylthio)-propylthio]propylthio-propane-1-thiol, 2,2'-thiodiethanethiol, 4,14-bis(mercaptomethyl)-3,6,9,12, 15-pentathiahectadecane-1,17-dithiol, 2-(2-mercaptoethylthio)-3-[4-(1-{4-[3-mercapto-2-(2-mercaptoethylthio)-propoxy]-phenyl}-1-methylethyl)-phenoxy]-propane-1-thiol, pentaerythritol tetrakis(3-mercaptopropionate), pentaerythritol mercaptoacetate, trimethanolpropanetrismercaptopropionate, glycerol trimercaptopropionate, dipentaerythritol hexamercaptopropionate, or 2,5-bismercaptomethyl-1,4-dithiane.

The thiol may be any one or two or more of the exemplary compounds, but it is not limited thereto.

In addition, specific examples of the episulfide include bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio) butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-f-epithiopropylthioethyl) thioethyl]thio]ethane, tetrakis(β-epithiopropylthiomethyl) methane, 1,1,1-tris(3-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl) thiomethyl]-3,7-ditianonane, 1,10-bis(β-epithiopropylthio)-5,6-bis[(2-β-epithiopropylthioethyl)thio]-3,6,9-trithiadecane, 1,11-bis(D3-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6, 9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, 2,5-bis(β-epithiopropylthioethylthiomethyl)-1,4-dithiane, 1,3-bis(β-epithiopropylthio)benzene, 1,4-bis(β-epithiopropylthio)benzene, 1,3-bis(β-epithiopropylthiomethyl)benzene, 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl] sulfone, and 4,4'-bis(β-epithiopropylthio)biphenyl.

The episulfide may be any one or two or more of the exemplary compounds, but it is not limited thereto. In addition, the episulfide may be a compound in which at least one of the hydrogens of its thioepoxy group is substituted with a methyl group.

The polymerizable composition for an optical material may comprise the diisocyanate composition and the thiol or episulfide in a mixed state or in a separated state. That is, in the polymerizable composition, they may be in a state of being compounded in contact with each other or separated from each other so as not to contact each other.

The polymerizable composition for an optical material may comprise the thiol or episulfide and the diisocyanate composition at a weight ratio of 2:8 to 8:2, 3:7 to 7:3, or 4:6 to 6:4.

A catalyst, a chain extender, a crosslinking agent, an ultraviolet stabilizer, an antioxidant, an anti-coloring agent, a dye, a filler, a release agent, and the like may be further added depending on the purpose when the polymerizable composition for an optical material and an optical material are prepared.

The thiol or episulfide is mixed with a diisocyanate composition and other additives, which is defoamed, injected into a mold, and gradually polymerized while the temperature is gradually elevated from low to high temperatures. The resin is cured by heating to prepare an optical material.

The polymerization temperature may be, for example, 20° C. to 150° C., particularly 25° C. to 120° C. In addition, a reaction catalyst, which is conventionally used in the production of polythiourethane, may be employed in order to control the reaction rate. Specific examples of the reaction catalyst are as exemplified above.

In addition, if required, the optical material thus prepared may be subjected to physical or chemical treatment such as anti-reflection coating, hardness, enhancements in abrasion resistance and chemical resistance, anti-fogging, surface polishing, antistatic treatment, hard coat treatment, anti-reflection treatment, and dyeing treatment.

[Optical Material]

The optical material according to an embodiment of the present invention comprises a polythiourethane polymerized from a diisocyanate composition and a thiol or an episulfide, wherein the content of a benzyl isocyanate having a methyl group is 5 ppm to 200 ppm, the content of an aromatic compound having a halogen group is 5 ppm to 1,000 ppm, or the content of a benzyl isocyanate having an ethyl group is 1 ppm to 1,000 ppm in the diisocyanate composition.

The optical material is not only excellent in transparency, refractive index, and yellow index, but also capable of enhancing the impact resistance and preventing striae and cloudiness.

For example, the optical material may have a refractive index of 1.55 or more, specifically a refractive index of 1.55 to 1.77. In addition, the optical material may have an Abbe number of 30 to 50, specifically 30 to 45 or 31 to 40. In addition, the optical material may have a light transmittance of 80% or more, 85% or more, or 87% or more, which may be a total light transmittance. In addition, the optical material may have a yellow index (Y.I.) of 30 or less, 25 or less, 22 or less, or 20 or less, for example, 1 to 25 or 10 to 22. Specifically, the optical material may have a transmittance of 85% or more and a yellow index of 22 or less.

In addition, the optical material may have excellent impact resistance energy within an appropriate range. The impact resistance energy may be measured as the potential energy of a weight that breaks a specimen prepared in the form of a plate having a diameter of 80 mm and a thickness of 1.2 mm when steel balls having different weights are fallen thereto in a sequence from a light ball to a heavy ball at a height of 127 cm at a temperature of 20° C. according to the test standards of the US FDA. Specifically, steel balls each having a weight of 16 g, 32 g, 65 g, 100 g, 200 g, or 300 g are used in the ball dropping test at various heights to measure the potential energy when an optical material, specifically an optical lens, is broken. For example, the potential energy (Ep) is 0.2 (J) (Ep=mgh=0.016×9.8×1.27=0.2 (J)) for 16 g and 127 cm according to the FDA standard. If a specimen passes the ball dropping test of a steel ball of 16 g, the potential energy (Ep) is then calculated using a steel ball of 32 g. If the specimen passes this test, steel balls each having a weight of 65 g, 100 g, 200 g, or 300 g are sequentially used to measure the potential energy when the specimen is finally broken.

The optical material according to an embodiment of the present invention has an excellent impact resistance energy (E) as measured by the above method, which is 0.3 J to 3.0 J, 0.4 J to 3.0 J, 0.4 J to 2.5 J, 0.6 J to 3.0 J, 0.6 J to 2.8 J, 0.8 J to 2.8 J, 0.8 J to 2.5 J, 0.4 J to 4.0 J, 0.4 J to 3.7 J, 0.6 J to 4.0 J, 0.6 J to 3.7 J, or 0.8 J to 1.6 J.

Thus, a diisocyanate composition comprising a specific content of a benzyl isocyanate having a methyl group, an aromatic compound having a halogen group, or a benzyl isocyanate having an ethyl group is used to prepared an optical material, thereby improving the optical characteristics by preventing the occurrence of yellowing, striae, and cloudiness and enhancing the mechanical properties such as impact resistance at the same time. It can be advantageously used to prepare high-quality eyeglass lenses, camera lenses, and the like.

Mode for Carrying Out the Invention

Hereinafter, more specific embodiments are illustrated, but the present invention is not limited thereto.

Example 1-1

<Step 1: Preparation of a Diamine Hydrochloride Composition>

A 5-liter, 4-neck reactor was charged with 1009.4 g (9.46 moles) of an aqueous solution of 35% hydrochloric acid, followed by lowering the internal temperature of the reactor to 15° with stirring. While the temperature of the reactor was maintained at lower than 60° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,320 g of tetrahydrofuran as an organic solvent was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

<Step 2: Preparation of a Diisocyanate Composition>

Reactor A was charged with 800 g of the m-XDA hydrochloride composition prepared above and 3,550 g of orthodichlorobenzene (ODCB), followed by elevating the internal temperature of the reactor to about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the organic solvent (ODCB) was removed, and m-XDI was purified by distillation under the following distillation conditions. The removal of the organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C. 3-methylbenzyl isocyanate was added after the distillation (second distillation) to obtain a m-XDI composition in which the concentration of 3-methylbenzyl isocyanate in the composition was adjusted to 5 ppm.

<Preparation of an Optical Material>

49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Examples 1-2 to 1-7

A m-XDI composition and an optical lens were obtained in the same manner as in Example 1-1, except that the timing and concentration of 3-methylbenzyl isocyanate introduced were adjusted as shown in Table 1 below.

Comparative Examples 1-1 to 1-7

A m-XDI composition and an optical lens were obtained in the same manner as in Example 1-1, except that the timing and concentration of 3-methylbenzyl isocyanate introduced were adjusted as shown in Table 1 below.

<Evaluation Method>

The Examples and the Comparative Examples were evaluated as follows.

(1) Refractive Index (Nd20)

The solid-phase refractive index (nd20) was measured at 20° C. using an Abbe refractometer DR-M4.

(2) Yellow Index (Y.I.) and Light Transmittance

An optical lens was prepared in the form of a cylinder with a radius of 16 mm and a height of 45 mm. Light was transmitted in the height direction to measure the yellow index and transmittance. The yellow index was calculated by the following equation based on the values of x and y, which are the measurement results.

$$Y.I.=(234x+106y)/y \qquad \text{[Equation 1]}$$

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Haze (Cloudiness)

The cured lens was irradiated to a projector in a darkroom to observe whether the lens was cloudy or had any opaque material with the naked eyes.

Cloudiness absent: the lens was not cloudy and had no opaque material

Cloudiness present: the lens was cloudy or had an opaque material (5) Impact Resistance The impact resistance was measured as the potential energy of a weight that broke a specimen prepared in the form of a plate having a diameter of 80 mm and a thickness of 1.2 mm when steel balls having different weights were fallen thereto in a sequence from a light ball to a heavy ball at a height of 127 cm at a temperature of 20° C. according to the test standards of the US FDA.

Steel balls each having a weight of 16 g, 32 g, 65 g, 100 g, 200 g, or 300 g were used in the ball dropping test at various heights to measure the potential energy when the lens was broken.

Calculation Example 1: The Potential Energy (Ep) for 16 g and 127 cm According to the FDA Standard $$Ep=mgh=0.016 \times 9.8 \times 1.27=0.2 \text{ (J)}$$

Calculation Example 2: The Potential Energy for 67 g and 127 cm According to the Industrial Safety Standards $$Ep=mgh=0.067 \times 9.8 \times 1.27=0.83 \text{(J)}$$

TABLE 1

| | m-xylylene diisocyanate (wt. %) | 3-methylbenzyl isocyanate | | Optical lens | | | | Impact resistance (J) |
| --- | --- | --- | --- | --- | --- | --- | --- | --- |
| | | Timing of introduction | Concentration of introduction | Stria | Cloudiness | Transmittance | Y.I. | |
| Ex. 1-1 | 99.9 | After distillation | 5 ppm | Absent | Absent | 91% | 19 | 0.4 J |
| Ex. 1-2 | 99.9 | Before mixing | 5 ppm | Absent | Absent | 91% | 19 | 0.4 J |
| Ex. 1-3 | 99.9 | After distillation | 20 ppm | Absent | Absent | 91% | 20 | 0.8 J |
| Ex. 1-4 | 99.9 | Before mixing | 20 ppm | Absent | Absent | 90% | 19 | 0.8 J |
| Ex. 1-5 | 99.9 | After distillation | 150 ppm | Absent | Absent | 90% | 19 | 1.2 J |
| Ex. 1-6 | 99.9 | Before mixing | 150 ppm | Absent | Absent | 89% | 20 | 1.2 J |
| Ex. 1-7 | 99.9 | After distillation | 200 ppm | Absent | Absent | 89% | 21 | 2.5 J |
| C. Ex. 1-1 | 99.9 | No addition | 0.0 | Absent | Absent | 91% | 20 | 0.2 J |
| C. Ex. 1-2 | 99.9 | After distillation | 1 ppm | Absent | Absent | 90% | 20 | 0.2 J |
| C. Ex. 1-3 | 99.9 | Before mixing | 1 ppm | Absent | Absent | 91% | 20 | 0.2 J |
| C. Ex. 1-4 | 99.9 | After distillation | 3-4 ppm | Absent | Absent | 91% | 20 | 0.2 J |
| C. Ex. 1-5 | 99.9 | Before mixing | 3-4 ppm | Absent | Absent | 91% | 19 | 0.2 J |
| C. Ex. 1-6 | 99.9 | After distillation | 220 ppm | Absent | Present | 84% | 20 | 2.5 J |
| C. Ex. 1-7 | 99.9 | Before mixing | 220 ppm | Absent | Present | 84% | 20 | 2.5 J |

As can be seen from the above table, the optical lenses prepared as an optical material using the diisocyanate compositions of the Examples of the present invention were excellent in impact resistance in an appropriate range as compared with the optical lenses of the Comparative Examples, and they had no striae and cloudiness.

Specifically, the optical lenses of Examples 1-1 to 1-7 had no striae and cloudiness, a high transmittance of 89% or more, allow yellow index, and an impact resistance as excellent as 0.4 J to 2.5 J.

Meanwhile, similar results were obtained regardless of whether 3-methylbenzyl isocyanate was added before the diisocyanate composition was mixed with a thiol or an episulfide or after distillation.

In contrast, in Comparative Examples 1-1 to 1-5 in which the content of 3-methylbenzyl isocyanate was 4 ppm or less, the impact resistance was very low as 0.2 J although striae and cloudiness did not occur.

Meanwhile, in Comparative Examples 1-6 and 1-7 in which the content of 3-methylbenzyl isocyanate was excessive as 220 ppm, cloudiness occurred, and the transmittance was very low as 85% or less.

Accordingly, the diisocyanate composition according to an embodiment of the present invention is excellent in optical characteristics as well as mechanical properties when applied to an optical lens. Thus, it is suitable for use as an optical lens of high quality.

Example 2-1

<Step 1: Preparation of a Diamine Hydrochloride Composition>

A 5-liter, 4-neck reactor was charged with 1009.4 g (9.46 moles) of an aqueous solution of 35% hydrochloric acid, followed by lowering the internal temperature of the reactor to 15° C. with stirring. While the temperature of the reactor was maintained at lower than 60° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,320 g of tetrahydrofuran as an organic solvent was introduced, and the internal temperature of the reactor was lowered to –5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

Step 2: Preparation of a Diisocyanate Composition

Reactor A was charged with 800 g of the m-XDA hydrochloride composition prepared above and 3,550 g of orthodichlorobenzene (ODCB), followed by elevating the internal temperature of the reactor to about 125° C. with stirring. Reactor B was charged with 950 g of triphosgene (BTMC) and 800 g of ODCB, which was stirred at about 60° C. for dissolution. While the temperature was maintained at 125° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the organic solvent (ODCB) was removed, and m-XDI was purified by distillation under the following distillation conditions. The removal of the organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C. 1,3-bis(chloromethyl)benzene was added after the distillation (second distillation) to obtain a m-XDI composition in which the concentration of 1,3-bis(chloromethyl)benzene in the composition was adjusted to 5 ppm.

<Preparation of an Optical Material>

49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Examples 2-2 to 2-12

A m-XDI composition and an optical lens were obtained in the same manner as in Example 2-1, except that the timing and concentration of 1,3-bis(chloromethyl)benzene introduced were adjusted as shown in Table 2 below.

Comparative Examples 2-1 to 2-7

A m-XDI composition and an optical lens were obtained in the same manner as in Example 2-1, except that the timing and concentration of 1,3-bis(chloromethyl)benzene introduced were adjusted as shown in Table 2 below.

<Evaluation Method>

The Examples and the Comparative Examples were evaluated as follows.

(1) Refractive Index (Nd20)

The solid-phase refractive index (nd20) was measured at 20° C. using an Abbe refractometer DR-M4.

(2) Yellow Index (Y.I.) and Light Transmittance

An optical lens was prepared in the form of a cylinder with a radius of 16 mm and a height of 45 mm. Light was transmitted in the height direction to measure the yellow index and transmittance. The yellow index was calculated by the following equation based on the values of x and y, which are the measurement results. Y.I.=(234x+106y)/y.

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Haze (Cloudiness)

The cured lens was irradiated to a projector in a darkroom to observe whether the lens was cloudy or had any opaque material with the naked eyes.

Cloudiness absent: the lens was not cloudy and had no opaque material

Cloudiness present: the lens was cloudy or had an opaque material (5) Impact Resistance The impact resistance was measured as the potential energy of a weight that broke a specimen prepared in the form of a plate having a diameter of 80 mm and a thickness of 1.2 mm when steel balls having different weights were fallen thereto in a sequence from a light ball to a heavy ball at a height of 127 cm at a temperature of 20° C. according to the test standards of the US FDA.

Steel balls each having a weight of 16 g, 32 g, 65 g, 100 g, 200 g, or 300 g were used in the ball dropping test at various heights to measure the potential energy when the lens is broken.

Calculation Example 1: The Potential Energy (Ep) for 16 and 7 cm According to the FDA Standard $$Ep=mgh=0.016 \times 9.8 \ 5 \ 1.27=0.2 \ (J)$$

Calculation Example 2: The Potential Energy for 67 g and 127 cm According to the Industrial Safety Standards $$Ep=mgh=0.067 \times 9.8 \times 1.27=0.83 \ (J)$$

TABLE 2

| | m-xylylene diisocyanate (wt. %) | 1,3-bis(chloromethyl)benzene | | Optical lens | | | | |
| | | Timing of introduction | Concentration of introduction | Stria | Cloudiness | Transmittance | Y.I. | Impact resistance |
| --- | --- | --- | --- | --- | --- | --- | --- | --- |
| Ex. 2-1 | 99.9 | After distillation | 5 ppm | Absent | Absent | 91% | 19 | 0.4 J |
| Ex. 2-2 | 99.9 | Before mixing | 5 ppm | Absent | Absent | 91% | 19 | 0.4 J |
| Ex. 2-3 | 99.9 | After distillation | 20 ppm | Absent | Absent | 91% | 20 | 0.8 J |
| Ex. 2-4 | 99.9 | Before mixing | 20 ppm | Absent | Absent | 91% | 19 | 0.8 J |
| Ex. 2-5 | 99.9 | After distillation | 150 ppm | Absent | Absent | 90% | 19 | 1.2 J |
| Ex. 2-6 | 99.9 | Before mixing | 150 ppm | Absent | Absent | 90% | 20 | 1.2 J |
| Ex. 2-7 | 99.9 | After distillation | 300 ppm | Absent | Absent | 89% | 21 | 2.5 J |
| Ex. 2-8 | 99.9 | Before mixing | 300 ppm | Absent | Absent | 89% | 21 | 2.5 J |
| Ex. 2-9 | 99.9 | After distillation | 500 ppm | Absent | Absent | 89% | 22 | 2.5 J |
| Ex. 2-10 | 99.9 | Before mixing | 500 ppm | Absent | Absent | 88% | 22 | 2.5 J |
| Ex. 2-11 | 99.9 | After distillation | 800 ppm | Absent | Absent | 88% | 22 | 3.7 J |
| Ex. 2-12 | 99.9 | After distillation | 1,000 ppm | Absent | Absent | 88% | 22 | 3.7 J |
| C. Ex. 2-1 | 99.9 | No addition | 0.0 | Absent | Absent | 91% | 20 | 0.2 J |
| C. Ex. 2-2 | 99.9 | After distillation | 1 ppm | Absent | Absent | 91% | 20 | 0.2 J |
| C. Ex. 2-3 | 99.9 | Before mixing | 1 ppm | Absent | Absent | 91% | 19 | 0.2 J |
| C. Ex. 2-4 | 99.9 | After distillation | 3-4 ppm | Absent | Absent | 91% | 19 | 0.2 J |
| C. Ex. 2-5 | 99.9 | Before mixing | 3-4 ppm | Absent | Absent | 91% | 20 | 0.2 J |
| C. Ex. 2-6 | 99.9 | After distillation | 1,100 ppm | Absent | Present | 84% | 24 | 3.7 J |
| C. Ex. 2-7 | 99.9 | Before mixing | 1,100 ppm | Absent | Present | 84% | 26 | 3.7 J |

As can be seen from the above table, the optical lenses prepared as an optical material using the diisocyanate compositions of the Examples of the present invention were excellent in impact resistance in an appropriate range as compared with the optical lenses of the Comparative Examples, and they had no striae and cloudiness with a reduced yellow index.

Specifically, the optical lenses of Examples 2-1 to 2-12 had no striae and cloudiness, a high transmittance of 88% or more, a low yellow index of 22 or lower, and an impact resistance as excellent as 0.4 J to 3.7 J.

Meanwhile, similar results were obtained regardless of whether 1,3-bis(chloromethyl)benzene was added before the diisocyanate composition was mixed with a thiol or an episulfide or after distillation.

In contrast, in Comparative Examples 2-1 to 2-5 in which the content of 1,3-bis(chloromethyl)benzene was 4 ppm or less, the impact resistance was very low as 0.2 J although striae and cloudiness did not occur.

Meanwhile, in Comparative Examples 2-6 and 2-7 in which the content of 1,3-bis(chloromethyl)benzene was excessive as 1,100 ppm, cloudiness occurred, and the transmittance was very low as 84% or less. In addition, the yellowness was also increased to 24 to 26.

Accordingly, the diisocyanate composition according to an embodiment of the present invention is excellent in optical characteristics as well as mechanical properties when applied to an optical lens. Thus, it is suitable for use as an optical lens of high quality.

Example 3-1

<Step 1: Preparation of a Diamine Hydrochloride Composition>

A 5-liter, 4-neck reactor was charged with 1009.4 g (9.46 moles) of an aqueous solution of 35% hydrochloric acid, followed by lowering the internal temperature of the reactor to 15° C. with stirring. While the temperature of the reactor was maintained at lower than 60° C., 600.0 g (4.4 moles) of metaxylylenediamine (m-XDA) was introduced for 1 hour. Upon completion of the introduction, the internal temperature of the reactor was lowered to 10° C., and it was stirred for 1 hour. Thereafter, 1,320 g of tetrahydrofuran as an organic solvent was introduced, and the internal temperature of the reactor was lowered to −5° C., followed by stirring for 1 hour. Upon completion of the reaction, it was subjected to vacuum filtration using a filter, and the filtered tetrahydrofuran was recovered for reuse. The recovery rate of the tetrahydrofuran was 82%. Upon the vacuum filtration, a metaxylylenediamine (m-XDA) hydrochloride composition was obtained. In order to remove the residual organic solvent and water, drying was performed under the conditions of a reactor external temperature of 90° C. and a vacuum pump of 0.1 Torr to obtain a final metaxylylenediamine (m-XDA) hydrochloride composition.

<Step 2: Preparation of a Diisocyanate Composition>

Reactor A was charged with 800 g of the m-XDA hydrochloride composition prepared above and 3,550 g of orthodichlorobenzene (ODCB), followed by elevating the internal temperature of the reactor to about 110° C. with stirring. Reactor B was charged with 950 g of triphosgene (BTMC) and 800 g of ODCB, which was stirred at about 60° C. for dissolution. While the reactor temperature was maintained at 110° C. so as not to precipitate, it was added dropwise to Reactor A over 24 hours. Upon completion of the dropwise addition, it was stirred for 4 hours. Upon completion of the reaction, nitrogen gas was blown into the solvent with bubbling at 125° C. to degas. It was cooled to 10° C., and the remaining solids were filtered using celite. Thereafter, the organic solvent (ODCB) was removed, and m-XDI was purified by distillation under the following distillation conditions. The removal of the organic solvent (first distillation) was carried out for 8 hours at a pressure of 0.5 torr or less and a temperature of 60° C. The distillation of m-XDI (second distillation) was carried out for 10 hours at a pressure of 0.1 torr or less and a temperature of 120° C. As a result, a m-XDI composition containing 59 ppm of a benzyl isocyanate having an ethyl group (1-ethyl-3-(isocyanatomethyl)benzene) was obtained.

<Preparation of an Optical Material>

49.3 parts by weight of 4,8-bis(mercaptomethyl)-3,6,9-trithiaundecane-1,11-dithiol, 50.7 parts by weight of the m-XDI composition prepared above, 0.01 part by weight of dibutyltin dichloride, and 0.1 part by weight of a phosphate ester release agent (ZELEC® UN Stepan) were homogeneously mixed, which was defoamed at 600 Pa for 1 hour, filtered through a Teflon filter of 3 μm, and injected into a mold made of a glass mold and a tape. The mold was maintained at 25° C. for 8 hours and slowly heated to 130° C. at a constant rate over 8 hours, and polymerization was carried out at 130° C. for 2 hours. The molded article was released from the mold and subjected to further curing at 120° C. for 2 hours to obtain an optical lens (or an optical material).

Examples 3-2 to 3-5

A m-XDI composition and an optical lens were obtained in the same manner as in Example 3-1, except that, in step 2, triphosgene (BTMC) and ODCB were added to reactor B, which was added dropwise to reactor A while the reactor temperature was maintained as shown in Table 3, thereby adjusting the content of 1-ethyl-3-(isocyanatomethyl)benzene in the composition.

Comparative Examples 3-1 to 3-3

A m-XDI composition and an optical lens were obtained in the same manner as in Example 3-1, except that, in step 2, triphosgene (BTMC) and ODCB were added to reactor B, which was added dropwise to reactor A while the reactor temperature was maintained as shown in Table 3, thereby adjusting the content of 1-ethyl-3-(isocyanatomethyl)benzene in the composition.

The reaction temperatures of the Examples and the Comparative Examples, m-XDI obtained therein, and the yield and purity are summarized in Table 3 below.

TABLE 3

| | Reaction temp. (temp. of dropwise addition) (° C.) | 1-ethyl-3-(isocyanatomethyl) benzene (ppm) | Before distillation (crude m-XDI) | | After distillation (m-XDI) | |
|---|---|---|---|---|---|---|
| | | | Purity (%) | Yield (%) | Purity (%) | Yield (%) |
| Ex. 3-1 | 110 | 59 ppm | 99.1 | 82 | 99.9 | 96 |
| Ex. 3-2 | 115 | 251 ppm | 99.2 | 85 | 99.9 | 96 |
| Ex. 3-3 | 120 | 422 ppm | 99.1 | 92 | 99.9 | 96 |
| Ex. 3-4 | 125 | 620 ppm | 99.0 | 93 | 99.9 | 94 |
| Ex. 3-5 | 130 | 985 ppm | 98.8 | 94 | 99.9 | 95 |
| C. Ex. 3-1 | 140 | 1,107 ppm | 98.5 | 94 | 99.8 | 95 |
| C. Ex. 3-2 | 150 | 1,356 ppm | 98.2 | 93 | 99.7 | 95 |
| C. Ex. 3-3 | 160 | 1,558 ppm | 98.1 | 93 | 99.6 | 95 |

<Evaluation Method>

The Examples and the Comparative Examples were evaluated as follows.

(1) Refractive Index (Nd20)

The solid-phase refractive index (nd20) was measured at 20° C. using an Abbe refractometer DR-M4.

(2) Yellow Index (Y.I.) and Light Transmittance

The optical lenses were each measured for chromaticity coordinates x and y using a spectrophotometer (Colormate, Scinco), from which their yellow indices were calculated with Equation 1 below. In addition, the transmittance at a wavelength of 550 nm was measured from the spectrum obtained using the same instrument.

$$Y.I.=(234x+106y+106)/y \qquad \text{[Equation 1]}$$

(3) Stria

A lens having a diameter of 75 mm with −2.00 and −8.00 D was prepared. Light from a mercury lamp as a light source was transmitted through the lens. The transmitted light was projected onto a white plate, and the presence or absence of contrast was visually checked to determine the generation of striae.

(4) Cloudiness

The cured lens was irradiated to a projector in a darkroom to observe whether the lens was cloudy or had any opaque material with the naked eyes.

Cloudiness absent: the lens was not cloudy and had no opaque material

Cloudiness present: the lens was cloudy or had an opaque material (5) Measurement of Gas Chromatography (GC)

Instrument: 6890/7890 of Agilent
Carrier gas: He
Injector: 250° C.
Oven: 40° C. to 320° C.
Column: HP-1, Wax, 30 m
Detector: FID, 300° C.

(5) Measurement of GC MS

Instrument: 7890B (GC), 5977A (MS) of Agilent
Mass range: 1.6 to 1,050 amu
Source: EI (electron ionization) (inert extractor EI source)
Mass spectrometer: quadrupole spectrometer
Oven: 40° C. (6 min)-10° C./min-140° C. (5 min)-15° C./min-290° C. (15 min)
Column: Rxi-5MS, ID 0.25 mm, L 30 m

TABLE 4

Properties of the optical material (lens)

| | Stria | Cloudiness | Transmittance | Yellow index (Y.I) | Refractive index |
|---|---|---|---|---|---|
| Ex. 3-1 | Absent | Absent | 91 | 20 | 1.669 |
| Ex. 3-2 | Absent | Absent | 90 | 19 | 1.669 |
| Ex. 3-3 | Absent | Absent | 91 | 20 | 1.669 |
| Ex. 3-4 | Absent | Absent | 90 | 70 | 1.669 |
| Ex. 3-5 | Absent | Absent | 91 | 20 | 1.669 |
| C. Ex. 3-1 | Absent | Present | 89 | 22 | 1.669 |
| C. Ex. 3-2 | Absent | Present | 85 | 23 | 1.669 |
| C. Ex. 3-3 | Absent | Present | 84 | 23 | 1.669 |

As can be seen from the above table, the optical lenses prepared as an optical material using the diisocyanate compositions of the Examples of the present invention were excellent in transmittance as compared with the optical lenses of the Comparative Examples, and they had no striae and cloudiness.

Specifically, the optical lenses of Examples 3-1 to 3-5 had no striae and cloudiness, a high transmittance of 91% or more, a low yellow index of 20 or lower, and an appropriate level of refractive index.

In contrast, in Comparative Examples 3-1 to 3-3 in which the content of 1-ethyl-3-(isocyanatomethyl)benzene exceeded 1,000 ppm, the optical lenses had cloudiness and a transmittance of 89% or less, which was significantly reduced as compared with the optical lenses of Examples 3-1 to 3-5.

Accordingly, the diisocyanate composition according to an embodiment of the present invention is excellent in optical characteristics as well as mechanical properties when applied to an optical lens. Thus, it is suitable for use as an optical lens of high quality.

The invention claimed is:

1. A composition comprising
    m-xylene diisocyanate in an amount of 99.5% by weight to less than 100% by weight based on the total weight of the composition; and
    a compound of Formula I in an amount of 5 ppm to 200 ppm by weight based on the total weight of the composition, a compound of Formula II in an amount of 5 ppm to 1,000 ppm by weight based on the total weight of the composition, a compound of Formula III in an amount of 1 ppm to 1,000 ppm by weight based on the total weight of the composition, or a combination thereof

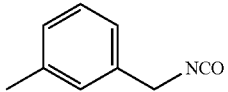

Formula 1

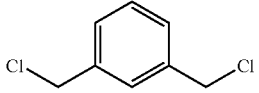

Formula 2

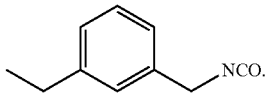

Formula 3

2. The composition of claim 1, further comprising p-xylylene diisocyanate in an amount of greater than 0% by weight to 0.5% by weight based on the total weight of the composition.

3. The composition of claim 1, further comprising a thiol or an episulfide.

4. An optical material comprising a cured product of a composition, the composition comprises
    m-xylene diisocyanate in an amount of 99.5% by weight to less than 100% by weight based on the total weight of the composition; and
    a compound of Formula I in an amount of 5 ppm to 200 ppm by weight based on the total weight of the composition, a compound of Formula II in an amount of 5 ppm to 1,000 ppm by weight based on the total weight of the composition, a compound of Formula III in an amount of 1 ppm to 1,000 ppm by weight based on the total weight of the composition, or a combination thereof

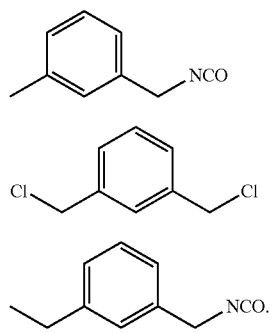
Formula 1
Formula 2
Formula 3
5. The optical material of claim 4, wherein the composition further comprises a thiol or an episulfide.
6. The optical material of claim 4, which has an impact resistance energy (E) of 0.4 J to 4.0 J, a transmittance of 90% or more, and a yellow index of 22 or less.
* * * * *